(12) United States Patent
van Groenestijn et al.

(10) Patent No.: US 6,709,592 B2
(45) Date of Patent: Mar. 23, 2004

(54) REMOVAL OF SULFUR COMPOUNDS FROM WASTEWATER

(75) Inventors: Johannes Wouterus van Groenestijn, Apeldoorn (NL); Josephus Sychbertus Adrianus Langerwerf, Doorwerth (NL)

(73) Assignee: Nederlandse Organisatie Voor Toegepast - Natuurwetenschappelijk Onderzoek Tno, Delft (NL)

( * ) Notice: Subject to any disclaimer, the term of this patent is extended or adjusted under 35 U.S.C. 154(b) by 0 days.

(21) Appl. No.: 10/204,634

(22) PCT Filed: Feb. 26, 2001

(86) PCT No.: PCT/NL01/00158
§ 371 (c)(1),
(2), (4) Date: Nov. 25, 2002

(87) PCT Pub. No.: WO01/62677
PCT Pub. Date: Aug. 30, 2001

(65) Prior Publication Data
US 2003/0141243 A1 Jul. 31, 2003

(30) Foreign Application Priority Data
Feb. 25, 2000 (EP) .............................................. 00200663

(51) Int. Cl.⁷ .............................. C02F 3/28; B01D 47/00
(52) U.S. Cl. ......................... 210/603; 210/631; 95/235; 423/243.01
(58) Field of Search ................................. 210/603, 612, 210/631; 95/158, 159, 235, 236; 423/243.01

(56) References Cited

U.S. PATENT DOCUMENTS 2,097,454 A * 11/1937 Fischer ........................ 423/220
5,354,545 A * 10/1994 Buisman ................... 423/242.1
5,474,682 A * 12/1995 Buisman ...................... 210/610
5,500,123 A    3/1996 Srivastava
5,922,204 A    7/1999 Hunter et al.
6,291,232 B1 * 9/2001 Miller, III .................... 435/262

FOREIGN PATENT DOCUMENTS

FR    2 741 874    6/1997

OTHER PUBLICATIONS

E. Sarner, "Removal of sulphate and sulphite in an anaerobic trickling filter", Water Science and Technology, vol. 22, No. 1–2, 1990, pp. 395–404.

* cited by examiner

Primary Examiner—Fred G. Prince
(74) Attorney, Agent, or Firm—Young & Thompson

(57) ABSTRACT

The invention relates to a process for removal of sulfur compounds from wastewater, which process provides recovery of elemental sulfur. The process is carried out in two separate anaerobic reactors. In the first reactor organic compounds are converted to acid compounds and sulfur compounds are converted to sulfide compounds. The sulfide compounds are stripped from said first reactor with a stripping gas. Subsequently, the effluent of the first reactor is fed to a second anaerobic reactor, in which organic compounds, such as the acid compounds, are converted to produce biogas, while any unconverted sulfur compounds from the previous step are converted to sulfide compounds as well. Finally, the sulfide compounds are removed from the second reactor in a stripping system, and converted to elemental sulfur in an adsorber.

12 Claims, 1 Drawing Sheet

REMOVAL OF SULFUR COMPOUNDS FROM WASTEWATER

FIELD OF THE INVENTION

The invention relates to a process for anaerobic removal of sulfur compounds from wastewater.

BACKGROUND OF THE INVENTION

Anaerobic biological processes for the treatment of wastewater having a high COD (chemical oxygen demand) value are known in the art. In such known processes, organic compounds are converted to biogas (a gas mixture comprising $CO_2$ and $CH_4$) at temperatures above about 25° C. When wastewater contains high amounts of sulfur compounds (e.g., more than ca. 100 mg $S/dm^3$), such as sulfates, problems may occur in operating such anaerobic reactors due to the presence of sulfide, which is formed under anaerobic conditions from sulfate. Sulfide may inhibit the methane formation. Also sulfide will give rise to $H_2S$ formation at pH<9. $H_2S$ is a toxic and corrosive gas and requires measures to control odour. The sulfide may be reoxidized into sulfate, but this requires an additional aerobic step. Furthermore, regulations often impose a strong limitation on the amount of sulfur compounds that can be discarded into the environment.

As a consequence, there is a need for processes to remove sulfide from wastewater. In the art different approaches have been suggested for sulfide removal processes. For example, EP-A-0 766 650 describes an anaerobic process in which $H_2S$ is stripped from a methanogenic reactor using a stripping gas. The $H_2S$ rich stripping gas is fed to a scrubber where the $H_2S$ is converted into elemental sulfur. The scrubber is operated with a regenerable redox liquid that contains an iron(III) chelate or an iron(III) complex. During this absorption process sulfide is converted to elemental sulfur, while Fe(III) is reduced to Fe(II). Fe(II) is reoxidized to Fe(III) by air in a separate aerator. This known process is particularly suited for the treatment of alkaline wastewater, such as tannery wastewater.

However, the known processes have a number of drawbacks.

The anaerobic reactor in known processes is operated at a relatively high pH (8–8.5), in particular when alkaline wastewater is treated having a pH of 9–12. As a result, the stripping of $H_2S$ is slow, since $H_2S$ dissolves more easily in water at higher pH. To compensate for this, equipment of a large volume has to be employed, in particular the stripper column, which has to be operated with large volumetric flows. An example of such a process employing an external stripper is found in U.S. Pat. No. 5,500,123. Alternatively, acid, such as formic acid, can be added. Both alternatives bring about high equipment and/or operating costs. Another result of operating the anaerobic reactor at a relatively high pH is that carbonate may precipitate in the stripper, which leads to fouling and clogging of the equipment.

When the $H_2S$ loaded gas is scrubbed in the known processes, inevitably an amount of $CO_2$, which is present in the stripped gas as well, is absorbed in the scrubber liquid. This $CO_2$ is eventually vented when the scrubber liquid is regenerated. This net removal of $CO_2$ from the system gives rise to a further increase of the pH. Moreover, the formation of carbonate salts due to the presence of $CO_2$ in the stripper equipment may give rise to fouling and clogging. The precipitation of carbonate salts may be prevented by lowering the pH, however, this lowers the rate of absorption and reaction of $H_2S$, as a result of which larger absorbers and volumetric flowrates are required.

These drawbacks become apparent for example in the process of EP-A-0 766 650, where the aqueous effluent needs to be recirculated over the stripper a number of times in order to lower the sulfide concentration, since per pass only a small amount of sulfide is stripped. This is the result of the unfavourable equilibrium at higher pH values. This recirculation results in further disadvantages, since the anaerobic reactor is operated at a higher hydraulic loading rate, which may lead to rinsing out of methanogenic sludge from the reactor.

Yet another disadvantage of known processes is that the elemental sulfur that is formed does not accumulate exclusively in the sulfur settling tank, but also forms deposits on walls of the tubing, vessels, sprayers, blowers, pumps, packing material, etc., which causes the need for regular cleaning of the equipment.

SUMMARY OF THE INVENTION

It is an object of the present invention to provide a process which obviates, at least partly, some or all of the above mentioned problems. The process of the invention thus aims to provide an improvement to anaerobic wastewater treatment with elemental sulfur recovery.

In accordance with the present invention, there is provided a process for removal of sulfur compounds from wastewater, comprising the steps of: a) converting in a first anaerobic suspended sludge reactor organic compounds present in the wastewater to acid compounds, forming an effluent comprising the acid compounds; b) converting the sulfur compounds to sulfide compounds in the first reactor, the remainder of the sulfur compounds being also comprised by said effluent; c) removing sulfide compounds in said first reactor with a stripping gas, forming a gaseous effluent; d) converting the acid compounds in said effluent to biogas in a second anaerobic reactor; and e) converting sulfur compounds in said effluent to sulfide compounds in the second anaerobic reactor, forming a second liquid effluent.

It will be understood that by converting the compounds in steps a), b), d) and e), and by stripping in step c) is meant that at least an essential part of the respective compounds present are converted, stripped or removed, the non-converted, non-stripped and non-removed compounds leaving the reactor in the effluent.

The organic compounds present in the wastewater are converted to acid compounds, in particular organic (carboxylic) acids, such as (lower) fatty acids. The conversion of organic compounds to acid compounds, as well as the conversion of sulfur compounds to sulfide is established using microorganisms known to the skilled person. For acidification of organic compounds bacterial species from the genera Clostridium, Ruminococcus, Propionibacterium, Selenomonas, Micromonospora, the family of the Lactobacteriaceae, and thermophilic clostridia can be used, as well as anaerobic sludge in which they are present. For the production of sulfide from sulfur compounds bacterial species from the genera Desulfovibrio, Desulfotomaculum, Desulfobacter, Desulfococcus, Desulfuromonas, Desulfonema, Desulfobulbus and for thermophilic applications *Sulfolobus* can be used, as well as sulfate reducing sludge or anaerobic sludge in which they are present.

The first (acidification) reactor typically works at 10–40° C. (mesophilic range) or 40–80° C. (thermophilic range), preferably 30–35° C., pressures between 0.3 and 4 bara, mostly 1 bara and biomass concentrations between 0.1 and 10 g dry weight/dm$^3$, mostly 3 g/dm$^3$. The ratio between stripping gas flow rate and wastewater flow rate can be 3 to 100, but is typically 15.

The term 'suspended sludge reactor' is used in the present description and claims in its ordinary meaning and encompasses, as the skilled person knows, reactors in which the sludge is essentially free to move through the reactor, viz. reactors in which the sludge is essentially not bound to a static surface in the reactor. Such reactors do therefore not rely on measures to increase the surface area which may serve as a substrate for the microorganisms, such as packings, etc. The sludge in these type of reactors is kept in suspension by means of agitation, e.g. by mixing using an agitator, by recirculating the liquids or by bubbling gas through the liquids.

As a result of the production of acid compounds, the pH in the first reactor will be relatively low. The pH in the first reactor will depend on the type of wastewater to be treated, but is generally maintained at a value lower than 9, preferably lower than 8, most preferably between 6 and 7.5. Because of the low pH, the sulfide formed in the first reactor is relatively easily stripped. Moreover, only a relatively small amount of $CO_2$ is formed. A substantial amount, typically about 50% or more, of the sulfur compounds is converted to sulfide, and 50–100% of the produced sulfide can be absorbed in an absorber. The non-absorbed sulfide is passed to the second reactor, as well as other sulfur compounds, if present.

Apart from acid compounds, the effluent from the first reactor may comprise other organic compounds, such as organic compounds that have not been converted in the first reactor or organic compounds that are intermediates from the reactions in the first reactor. Essentially all types of organic compounds may be converted to biogas in the second anaerobic (methanogenic) reactor. The conversion to biogas, as well as the conversion of remaining sulfur compounds in this second reactor is established using microorganisms known to the skilled person. The bacterial species that are typically employed for conversion of sulfur compounds were mentioned above as typical species for converting sulfur in the first reactor. For methane production bacterial species from the genera Methanococcus, Methanobacterium, Methanocarcina, Methanothrix, Methanophanus and Methanobrevibacter can be used. For thermophilic applications *Methanobacterium thermoautotrophicum* or species from Methanothermus can be used, as well as anaerobic sludge in which they are present The second (methanogenic) reactor typically works at 10–40° C. (mesophilic range) or 40–80° C. (thermophilic range), preferably 30–35° C., pressures between 0.3 and 4 bara, mostly 1 bara and biomass concentrations between 1 and 50 g dry weight/dm$^3$, mostly 30 g/dm$^3$. The ratio between stripping gas flow rate and wastewater flow rate can be 3 to 100, but is typically 20.

The sulfide loaded stripping gas leaves the first reactor and is processed in an absorber unit. A suitable absorber unit is described in EP-A-0 766 650 as mentioned herein-above. In detail, $H_2S$ is absorbed from a gaseous stream by contacting the gas with a regenerable redox liquor, having a pH from about 4 to 7. Preferably, the liquor comprises a transition metal complex, such as an Fe(III) complex, or chelated iron, such as ethylenediamine tetra-acetic acid (EDTA). The metal complex is preferably used in a concentration of about 0.01 to about 0.1 M.

Alternatively, the absorption of sulfide may be carried out with an alkaline scrubber, in which the gas is contacted with an alkaline solution and the $H_2S$ is converted to alkalihydrosulfide. The hydrosulfide may be converted to alkalisulfide (e.g. $Na_2S$), which may be reused in e.g. a tannery process. This type of $H_2S$ absorber is particularly preferred for tannery wastewater treatment processes according to the invention, since $Na_2S$ is used as a raw material in tanneries.

The low $CO_2$ production in the first reactor is very favourable. Since only little $CO_2$ is produced, the sulfide loaded stripping gas will be relatively low in $CO_2$ content. As a result, the sulfide may be removed from the gas, using means such as a conventional alkaline scrubbing process. If $CO_2$ were to be produced in substantial amounts, this would be removed by the alkaline solution as well. This would result in high alkali consumption in the absorber and in a net removal of $CO_2$ from the first reactor, leading to increased pH values in this reactor. For this reason, the low production of $CO_2$ is a considerable advantage of the present invention.

Preferably the process of the invention further comprises a step f) for removing the sulfide compounds from the second effluent (i.e. the liquid effluent from the second reactor) with a stripping system. Again, by removing in step f) is meant that at least an essential part of the sulfide present is removed, the non-removed sulfide leaving the reactor in the effluent. By removing a substantial amount of sulfide in the first reactor, removal of sulfur compounds in the form of sulfide can be carried out more easily in the second reactor, since the concentration of sulfide in the effluent of the first reactor is already significantly lower. Typically, about 50% of the sulfur present in the wastewater is removed. Moreover, the methanogenesis process in the second reactor will be less influenced by the presence of sulfide. The use of two separate anaerobic reactors is thus advantageous, since it is not required to return desulfidized water to the methanogenic reactor to decrease sulfide concentration. This prevents (1) a too high hydraulic loading rate in this reactor and as a consequence (2) risk of sludge wash out, as well as (3) lower methanogenic activities. This is in particular important for wastewater types which do not lead to granular sludge formation in methanogenic reactors, but to the formation of flocculant sludge, e.g. tannery wastewater.

Another important aspect of the present invention is that the sulfide is removed from the first reactor by feeding a stripping gas through the liquid in the reactor, e.g. by bubbling. This makes the use of an external stripper superfluous, thus saving on installation and operation costs. Also, by using a stripping gas, no $H_2S$ will accumulate in the headspace of the first reactor, which would occur when the liquid was fed to an external stripper.

In this respect, mention is made of U.S. Pat. No. 4,614,588, which describes a method for reducing the sulfur content of wastewater by employing two reactors. Sulfide is removed by exhausting the gas from the first reactor. To obtain sufficient separation of $H_2S$ gas (i.e. to produce sufficient $H_2S$ pressure in the head space of the reactor), it is required in the process of U.S. Pat. No. 4,614,588 that the pH is kept below 6. Such a requirement poses a strong limitation on the versatility of the removal process, since alkaline wastewater, e.g. tannery wastewater, cannot suitably be treated in such a process, since it would lead to a pH of higher than 6.

Another advantage of flowing stripping gas through the first reactor is that it enables a good mixing of the water, the anaerobic sludge flocs and the gas, whereby the sludge may be suspended in the water by the gas. This enables the use of the anaerobic contact process (ACP). This feature is specifically constitutes an advantage over the disclosure of U.S. Pat. No. 4,735,723, which describes a process for the removal of sulfur compounds from wastewater using two anaerobic reactors. According to this document, a fluidized bed reactor is preferred to carry out the acidification reaction, preferably combined with an external stripper. In fluidized bed reactors a high sludge age is employed. As a result of the high sludge age, microorganisms will develop that will convert organic acids to methane. As a result, the pH of the first reactor will increase, which is undesirable as was set out above. Sludge ages that are typical for fluidized bed reactors are generally too high for the process of the present invention. The reactor systems suggested in U.S. Pat. No. 4,735,723 separate all water and sludge in the reactor, as a result of which the sludge remains in the reactor for a period of time that is generally too high for the process of the present invention.

According to the present invention it is essential that the average sludge age is kept low, preferably below 5 days, more preferably from 1–4 days, most preferably at about 3 days.

This can be obtained by carrying out the separation of water and sludge in an external separator. This can be obtained by using the ACP process, which forms a preferred embodiment of the invention, especially for the treatment of alkaline wastewater.

In the ACP process wastewater is mixed with recycled sludge solids and then converted in a reactor sealed off from the entry of air. The contents of the reactor are completely mixed and the sludge is present in the form of suspended flocs. The flocs are kept in suspension by agitation. In the reactor the bacteria in the flocs biologically convert the compounds in the wastewater to other compounds. After the reaction, the mixed liquor, containing sludge flocs, is transported to a settling tank in which the flocs settle and the relatively clear supernatant is the effluent. At the bottom section of the settler a more concentrated suspension of flocs is formed. A large part of this suspension is recycled to the reactor, a smaller part is discharged. By settling and recycling, the formation of flocs by biomass in the system is promoted (by selection). Because of the completely mixed characteristics of the system, the sludge retention time (sludge age) can be controlled precisely by the discharge flow rate of the settled sludge. For example, if every day one-third of the total mass of sludge is removed from the system, the sludge age will be 3 days. Since acetoclastic methanogens (which convert acetic acid into methane) need sludge ages of more than 5 days (because of their high doubling time), they will not grow in a system with a sludge age of 3 days.

The ACP process is typically used for wastewater with COD concentrations of 1500–5000 mg/l and the hydraulic retention time is typically 2–10 hours. Although problems have been reported with separation of sludge and gas in methanogenic anaerobic contact processes, in the present non-methanogenic system a better separation is obtained, as the gas is not produced in the flocs but added in form of bubbles in the water phase.

Since the methanogenesis from fatty acids is minimized using the ACP process, an optimal accumulation of fatty acids and a corresponding low pH is obtained.

Other types of reactors known in the art are less or not suitable to obtain a suitable sludge age. For example, packed bed reactors, such as anaerobic filter or fixed film reactors, do not enable the control of sludge age, since in these reactors the biomass (from which the sludge is formed) is fixed to the packing.

In this respect, reference is made to a publication by E. Särner (*Wat. Sci. Tech.*, 22 (1990) 395–404), which describes a sulphur removal process that uses an anaerobic trickling filter (Antric filter as a pretreatment step. The pH in this step is kept low by applying a recirculation stream over the filter. The accumulation of organic acids leads to a pH lower than 6, the minimum pH for methanogenesis. However, such low pH cannot be guaranteed in case alkaline wastewater is treated. Than the high pH and the high sludge age will lead to conversion of organic acids into methane. In addition, even under low pH conditions, methanogenic activity can occur in the Antric filter; according to Särner, the choice for biofilm processes results in considerable $CH_4$ formation, since it is inevitable that at different biofilm depths, different environmental conditions are found, among which conditions that give rise to breakdown of organic acids, whereby $CH_4$ is produced. In addition, breakdown of organic acids results in a rise of pH, which makes this process unsuitable for treatment of alkaline waste water.

Also fluidized bed reactors are less suitable or even unsuitable, since these type of reactors are characterized by a considerable spread in residence time of the biomass. When fluidized support particles, such as sand, need to be partly refreshed, a portion of support particles covered with sludge will remain in the reactor. As the biomass growth on the fresh sand particles will be much slower than growth on the particles already covered with biomass, a large spread in sludge age will develop. As a result a considerable amount of biomass with a very high sludge age will be present in the reactor, which makes the development of acetoclastic methanogens possible, which results in the consumption of acetic acid.

Carrying out the desulfurization process in two separate reactors according to the invention, does not affect significantly the installation costs of the total plant.

By carrying out the process in accordance with the invention, the problem of precipitation of carbonate salts in the stripper as used in known processes is overcome. As a result of the lower pH, a lower flowrate of the stripping gas can be employed as well as a lower gas/liquid exchanging surface, making the need for an external (packed) stripper, operated with gas as the continuous phase unnecessary.

The biogas that is produced in the second reactor, will contain sulfide as well, which has to be removed. This can be done by conventional means, such as by the method described in EP-A-0 766 650, which was described hereinabove as a means to remove the sulfide from the product gas of the first reactor. By removing the sulfide from the product gas, clean biogas is obtained, which can be used for a variety of purposes, which will be apparent to the skilled person. The sulfide is converted in the absorber to elemental sulfur. The sulfur containing effluent of the absorber is fed through conventional means, such as a coagulator, a flocculator and/or a settling tank to produce a sulfur slurry, which also can be used for a variety of purposes, which will be apparent to the skilled person.

The liquid effluent of the second reactor may still contain a considerable amount of sulfide. These sulfide compounds can be removed from the liquid effluent, using a stripping column, which is fed with a stripping gas comprising $CO_2$. The stripping gas is brought into contact with the liquid by any suitable means, such as spraying or trickling the liquid down and flowing the stripping gas in countercurrent. The sulfide loaded stripping gas is then fed to an absorber unit, which is similar to the one described above, to convert the sulfide to elemental sulfur. The remaining desulfidized gas is vented.

Stripping of $H_2S$ from liquids proceeds more easily, i.e. at higher rates and/or more favorable equilibrium conditions, at relatively low pH (pH about 6.5 to 7.5) and higher temperatures (about 30–40° C., preferably at about 31–35, most preferably at about 33° C., instead of about 25° C.). For this reason it is preferred to use a combustion off-gas as the stripping gas in stripping the $H_2S$ from the liquid effluent of the second reactor. The $CO_2$ in the combustion off-gas provides a lower pH to the liquid, which enhances $H_2S$ stripping and prevents the formation of carbonate deposits in the stripper, whereas the heat present in the off-gas provides a higher temperature for the stripping process.

The combustion gases can be an effluent from conventional combustion processes. Another advantage of this embodiment is that no extra measures have to be taken to obtain $CO_2$ externally. It is preferred to use biogas produced with the process of the invention for producing the off-gases, since it can be burned on-site to produce these off-gases.

In addition, it was surprisingly found that, despite the lower solubility of $H_2S$ in Fe(III)chelate containing liquors, the higher temperatures of the sulfide loaded stripping gas, which results in an increased temperature in the absorber, the rate of $H_2S$ absorption is enhanced in the absorption step. Also the flocculation of sulfur is enhanced by higher temperatures, as will be discussed below.

In a further preferred embodiment of the invention, the removing of the sulfide in step f) comprises contacting the liquid effluent from the second reactor with an oxygen containing gas, preferably air. Thus the stripping of the liquid effluent from the second reactor is carried out using a gas mixture, which further comprises oxygen. The oxygen concentration will generally be up to 20 vol. %. Preferably the oxygen concentration is from 5–20 vol. %, most preferably about 14 vol. %. To this end air can be mixed with the stripping gas, such as the off-gas mentioned above. In the process described in EP-A-0 766 650 the reduction of Fe(III) to Fe(II) by sulfide (by which sulfur is produced) and the reoxidation of Fe(II) is carried out by separate processes, i.e., in separate columns. According to EP-A-0 766 650 the oxygen concentration has to be carefully controlled in order to prevent introduction of oxygen in the system. It is therefore surprising that according to the present process it is not required to operate the absorption of sulfide in the absence of oxygen. The oxygen which is introduced through the stripping column in the absorber can instead be used to regenerate the Fe(II) to Fe(III) (or another suitable redox system that is used) in the absorber. This makes the presence of a regenerator no longer required in this embodiment. Also means to control the oxygen concentration are no longer required, adding to the economic advantage of this embodiment.

A further preferred embodiment which uses oxygen to regenerate the redox liquor, comprises feeding the sulfide from the gaseous effluent from the second reactor and the sulfide from the liquid effluent from the second reactor to separate absorbers using the same recirculating redox liquor, in which the sulfide from said gaseous effluent from the second reactor is contacted with said redox liquor in co-current. The stream of biogas is essentially smaller than the gaseous effluent of the stripper used to treat the liquid effluent of the second reactor. Therefore the absorber treating the biogas can be smaller as well. However, the same absorption liquid may be used, provided that transfer of oxygen from freshly regenerated redox liquor to the biogas is prevented. This can be obtained by operating the absorber for the biogas such that the biogas and the regenerated absorption liquid flow in co-current. The oxygen present in the absorption liquid thus can react with the reduced metal (e.g. Fe(II) is oxidized to Fe(III)).

In another preferred embodiment, the liquid effluent of the second reactor is passed over a stripper only once. In conventional processes the sulfide containing effluent of a methanogenic reactor has to be recirculated over a stripper in order to obtain an acceptable decrease in sulfide concentration. This is also caused by the unfavorable chemical equilibrium as a result of the high pH employed. A disadvantage of recirculation of the aqueous effluent is that the higher hydraulic loading rate of the stripper requires a larger stripper. The second prerequisite for a smaller stripper is that no recirculation of stripper effluent over the methanogenic reactor is required, which bears the disadvantage of too high hydraulic loading rates and sludge wash out. According to the present invention, however, recirculation is not required, since a substantial amount of sulfide is already removed in the first reactor (up to about 50%), as a result of which, the methanogenesis in the second reactor is hardly adversely affected. By using a suitable stripping gas, such as $CO_2$ as described above, an overall sulfur removal of more than 90% can be obtained with the process of the invention, using no recirculation in the stripper for the liquid effluent of the second reactor.

Another preferred embodiment of the process of the invention is any of the processes as described above, in which step f) comprises contacting the sulfide containing biogas effluent and/or a gaseous sulfide containing effluent obtained from stripping the liquid effluent of the second reactor with a redox liquor at a pH of 7–9, preferably at a pH of about 8.5. In the art a pH of 4–7 is said to be optimal for operating the absorption step with a redox liquor, in order to minimize absorption of $CO_2$ from the sulfide containing gas. If net removal $CO_2$ from the system takes place, it is required to replenish it from external sources in order to prevent a pH that would be too high for operating the anaerobic reactor and the stripping process successfully. It was found, however, that the absorption of sulfide is enhanced when a higher pH of the redox liquor is employed. When a pH of about 7–9, preferably of about 8.5 is used, both the rate of absorption of $H_2S$ and the rate of conversion to elemental sulfur are increased. When conventional phosphate buffers are used in this liquor, this will give rise to considerable $CO_2$ losses. However, when bicarbonate buffers are used, preferably in concentration of 0.5–1 M, $CO_2$ losses can be prevented even at relatively high gas phase $CO_2$ concentrations expected (about 10%).

In another preferred embodiment, step f) comprises contacting the sulfide containing biogas effluent and/or a gaseous sulfide containing effluent obtained from stripping the liquid effluent of the second reactor with a redox liquor, by which sulfide is converted to sulfur, forming a sulfur comprising effluent, which is fed to a coagulation tank, a flocculation tank and a settler tank, thus forming a sulfur rich effluent. It was found that deposition of solid sulfur on equipment, such as tubing, vessel, gas blowers, pumps and packing material, can be prevented by removing the sulfur as quickly as possible from the redox liquor. To this end the redox liquid is first fed to the coagulation tank, in which it is stirred vigorously for about 1–3 minutes, giving rise to the formation of small sulfur crystals After the coagulation tank the liquid is fed to a flocculation tank in which the suspension is stirred mildly for 3–10 minutes, by which the crystals will form larger flocs. Flocculation can further be enhanced by the addition of conventional flocculation agents. The flocs formed can be removed easily by means of the settler tank to which the liquid is fed next. It was further found that coagulation of sulfur crystals proceeds more rapidly at elevated temperatures, which constitutes another advantage for the use of off-gases from combustion processes.

The process of the invention is particularly useful in treating wastewater with high COD concentrations (>2000 mg/dm$^3$).

Figure 1:
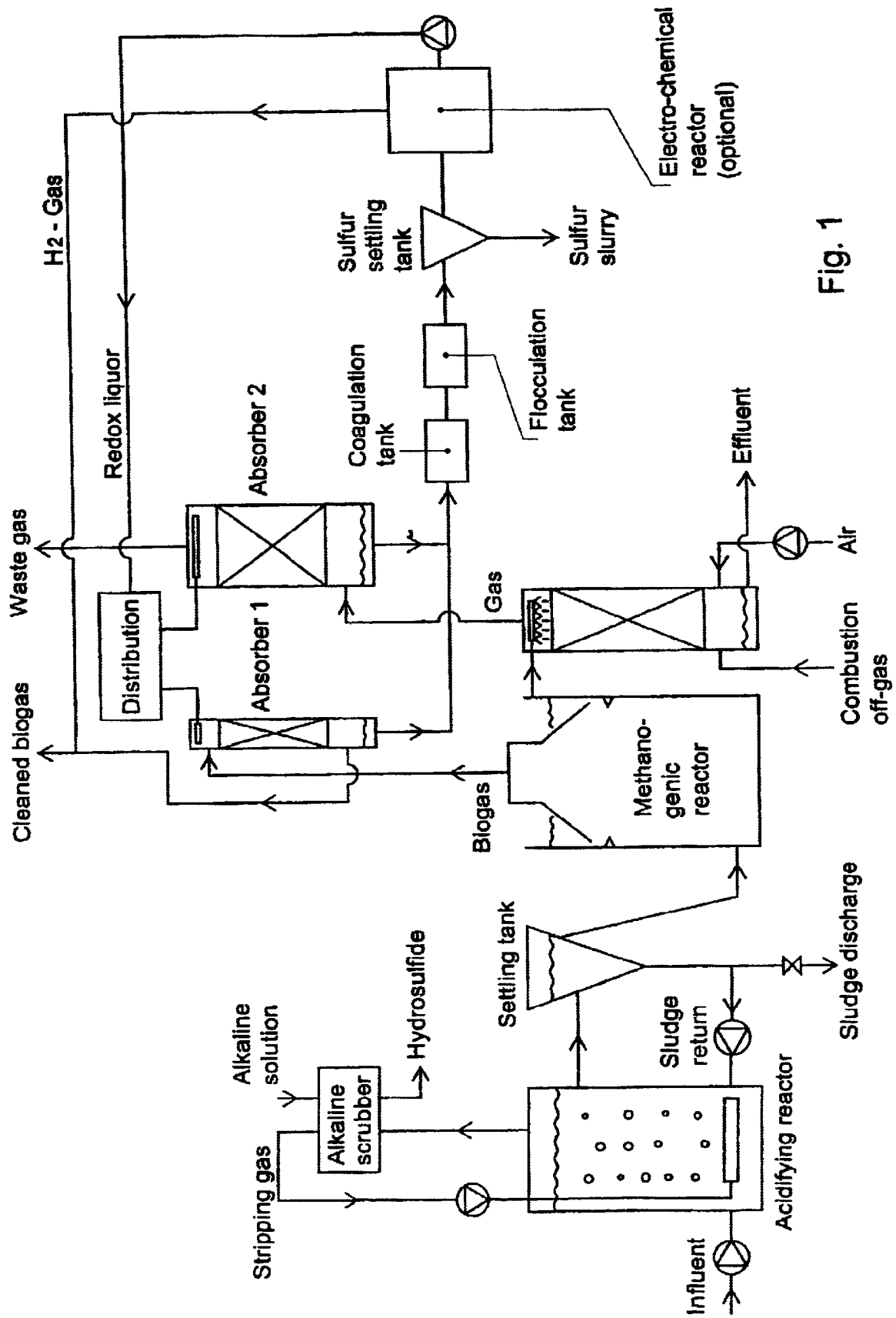
FIG. 1 describes a preferred embodiment of the process of the invention.

This process uses an alkaline scrubber to remove sulfide from the stripping gas in the first reactor. A wastewater influent is fed to a first (acidifying) reactor. By bubbling stripping gas through the first reactor the sulfide produced in the first reactor is stripped from the reactor. In the alkaline scrubber the stripping gas is desulfidized by contacting it with an alkaline solution. This produces a stream comprising hydrosulfide, which can be used for further processing and clean stripping gas which is recycled to the bottom of the first reactor. To prevent underpressure in the stripping gas recycle of the first reactor (e.g. as a result of absorption of gases in the reactor) or overpressure in this reactor (e.g. as a result of methane production), it may be useful to connect this stripping gas circuit with the biogas effluent from the second reactor. The liquid effluent from the first reactor is passed to a settler tank, in which the sludge settles and is recirculated to the reactor, while the liquid is fed to the second (methanogenic) reactor. The liquid effluent of the second reactor is sprinkled from the top of a stripper column, which is fed at the bottom with a mixture of combustion off-gas and air. The liquid effluent of this stripping column, which is essentially desulfurized may be discharged. The biogas produced in the second reactor is passed to the top of an absorber (Absorber 1) in which it is contacted in co-current with fresh redox liquor. The purified biogas leaves Absorber 1 at the bottom. Optionally it can be mixed with hydrogen gas. This hydrogen gas can be produced by an electrochemical reactor, as is described in EP-A-0 766 650. The stripping gas from the stripper which is used to desulfidize the liquid effluent of the second reactor is fed to another absorber (Absorber 2). In Absorber 2 the sulfide loaded stripping gas is brought into contact with a fresh redox liquor to convert sulfide to sulfur. Absorber 2 is operated in countercurrent. The purified gas leaving at the top of absorber 2 is vented. The redox liquors in both absorbers are obtained from the same recirculating system. The bottom products of the absorbers, containing elemental sulfur, are fed to a coagulation tank, a flocculation tank and to a sulfur settling tank. The sulfur is obtained as a slurry from the bottom of the settling tank.

EXAMPLES

Example 1

An anaerobic reactor of 5l was fed with tannery wastewater with a pH of 10. The wastewater contained 3500 mg COD, 50 mg sulfide and 1350 mg sulfate per liter, and was added at a flow rate of 40 l/day. The sludge residence time was higher than the hydraulic residence time in the reactor because of sludge sedimentation in the bottom part of the reactor. By daily removing ⅓ of the sludge present, the sludge age was set at 3 days. In the top of the reactor gas was sparged, after leaving the reactor the gas was bubbled through a solution of NaOH at a pH of 10 and returned to the reactor sparger again. The gas flow rate was 100 l/h.

The effluent of the reactor contained 3200 mg COD, 2000 mg VFA (volatile fatty acids), 150 mg sulfate and 30 mg sulfide per liter, and the pH was 7.3. The H$_2$S concentration in the gas leaving the reactor was 6400 ppm and after passing the absorber, the concentration was 3500 ppm. The CO$_2$ concentration in the gas was 1.5% and 1.3% after the absorber.

The results indicate that a large part of the organic compounds are converted into volatile fatty acids and that because of a low methanogenic activity the acids were allowed to accumulate, thus leading to a low pH and enhancing the stripping process. Simultaneously about 90% of the sulfate was reduced to sulfide. This sulfide was removed for 90% by stripping and absorption. The alkali scrubber relatively (%) removed more H$_2$S than CO$_2$.

Example 2

In a pilot plant H$_2$S rich gas was produced in a stripper by contacting the gas with effluent from an anaerobic reactor. This gas was passed through a 3 m$^3$ absorber column with a height of 3.5 m, counter-current with a redox liquor flow of 5 m$^3$/h. The redox liquor was trickled over the plastic column packing material and contained Fe(III)EDTA as the main reactant. Its pH was varied using NaOH and CO$_2$. Two different gas loading rates were tested (50 and 100 m$^3$/h). The temperature was 30° C. The results are summarised in table 1.

TABLE 1

H$_2$S removal efficiencies in an absorber at various conditions

| Gas flow rate (m$^3$/h) | pH of redox liquor | H$_2$S in absorber influent gas (ppm) | H$_2$S in absorber effluent gas (ppm) | H$_2$S removal efficiency (%) |
|---|---|---|---|---|
| 50 | 7.3 | 25,000 | 600 | 97.6 |
| 50 | 7.7 | 30,000 | 440 | 98.5 |
| 50 | 8.0 | 10,000 | 175 | 98.3 |
| 100 | 7.5 | 10,000 | 775 | 92.3 |
| 100 | 7.9 | 9,000 | 400 | 95.6 |
| 100 | 8.0 | 7,000 | 300 | 95.7 |
| 100 | 8.3 | 14,000 | 425 | 97.0 |
| 100 | 8.4 | 9,000 | 300 | 96.7 |

A higher pH is beneficial to reach lower effluent H$_2$S concentrations and/or higher H$_2$S removal efficiencies. Because of the higher gas residence times in the absorber column, higher removal efficiencies were obtained at lower gas flow rates.

What is claimed is:

1. Process for removal of sulfur compounds from wastewater, comprising the steps of:
   a) converting in a first anaerobic suspended sludge reactor organic compounds present in the wastewater to acid compounds, forming an effluent comprising the acid compounds;
   b) converting the sulfur compounds to sulfide compounds in the first reactor, the remainder of the sulfur compounds being also comprised by said effluent;
   c) removing sulfide compounds in said first reactor with a stripping gas, forming a gaseous effluent;
   c2) concentrating said effluent, thus forming a clearer effluent and a more concentrated suspension of sludge, part of which suspension is recycled to said first reactor;
   d) converting the acid compounds in said clearer effluent to biogas in a second anaerobic reactor; and
   e) converting sulfur compounds in said clearer effluent to sulfide compounds in the second anaerobic reactor, forming a second liquid effluent.

2. Process according to claim 1, which further comprises a step f) of removing the sulfide compounds from said second effluent with a stripping system.

3. Process according to claim 2, wherein the removing of the sulfide in step f) comprises contacting the liquid effluent from the second reactor with a stripping gas comprising $CO_2$, which is an off-gas from a combustion process.

4. Process according to claim 2, wherein step f) comprises stripping the liquid effluent from the second reactor without recycling the liquid.

5. Process according to claim 2, wherein step f) comprises contacting the containing biogas effluent and/or a gaseous sulfide containing effluent obtained from stripping the liquid effluent of the second reactor with a redox liquid at a pH of 7–9, which redox liquor comprises a bicarbonate buffer.

6. Process according to claim 2, wherein step f) comprises contacting the sulfide containing biogas effluent and/or a gaseous sulfide containing effluent obtained from stripping the liquid effluent of the second reactor with a redox liquor, by which sulfide is converted to sulfur, forming a sulfur comprising effluent, which is fed to a coagulation tank, a flocculation tank and a settler tank, thus forming a sulfur rich effluent.

7. Process according to claim 2, wherein the removing of the sulfide in step f) comprises contacting the liquid effluent from the second reactor with an oxygen containing gas, producing a sulfide containing gaseous effluent and feeding this gasous effluent to an absorber in which it is contacted with a redox liquor, which absorbs the sulfide.

8. Process according to claim 7, wherein the sulfide from the biogas effluent from the second reactor and the sulfide stripped from the liquid effluent from the second reactor are absorbed in separate absorbers using the same recirculating redox liquor, and wherein the sulfide from said gaseous effluent from the second reactor is contacted with said redox liquor in co-current.

9. Process according to claim 1, in which the gaseous effluent of step c) is contacted with a redox liquor or an alkaline solution, thereby removing sulfide from the gaseous effluent and producing clean stripping gas which is recirculated to the process in step c).

10. Process according to claim 1, wherein the sludge age in the first reactor is from 1–4 days.

11. Process according to claim 1, wherein an anaerobic contact process (ACP) is carried out in the first reactor.

12. Process according to claim 1, which further comprises: g) contacting the biogas from step d) with a redox liquor, which absorbs sulfide in the redox liquor; h) regenerating the redox liquor by contacting it with an oxygen containing gas.

* * * * *